(12) United States Patent
Polefko et al.

(10) Patent No.: US 9,098,610 B2
(45) Date of Patent: Aug. 4, 2015

(54) COMMUNICATION FOR IMPLANTABLE MEDICAL DEVICES

(75) Inventors: Richard J. Polefko, Parma, OH (US); David J. Howard, North Ridgeville, OH (US); Scott G. Leyh, Cleveland Heights, OH (US); Steven E. Wilder, Ashland, OH (US)

(73) Assignee: Greatbatch Ltd., Clarence, NY (US)

( * ) Notice: Subject to any disclaimer, the term of this patent is extended or adjusted under 35 U.S.C. 154(b) by 192 days.

(21) Appl. No.: 13/334,361

(22) Filed: Dec. 22, 2011

(65) Prior Publication Data

US 2013/0166642 A1  Jun. 27, 2013

(51) Int. Cl.
*G06F 15/16* (2006.01)
*G06F 19/00* (2011.01)
*G06Q 10/10* (2012.01)

(52) U.S. Cl.
CPC ........... *G06F 19/3418* (2013.01); *G06Q 10/10* (2013.01)

(58) Field of Classification Search
CPC ............ G06Q 10/10; H04L 29/08072; H04L 29/0809; H04L 29/06
USPC .................................................. 709/203, 204
See application file for complete search history.

(56) References Cited

U.S. PATENT DOCUMENTS

| | | | |
|---|---|---|---|
| 5,342,408 A * | 8/1994 | deCoriolis et al. | 607/32 |
| 5,902,949 A * | 5/1999 | Mohrbacher | 84/609 |
| 7,177,690 B2 * | 2/2007 | Woods et al. | 607/29 |
| 7,254,448 B2 | 8/2007 | Almendinger et al. | |
| 7,269,186 B2 * | 9/2007 | Abrol et al. | 370/476 |
| 7,347,819 B2 * | 3/2008 | Lebel et al. | 600/300 |
| 7,457,669 B2 * | 11/2008 | Katoozi et al. | 607/60 |
| 7,519,430 B2 * | 4/2009 | Von Arx et al. | 607/60 |
| 7,574,266 B2 | 8/2009 | Dudding et al. | |
| 7,743,151 B2 * | 6/2010 | Vallapureddy et al. | 709/227 |
| 7,755,527 B2 * | 7/2010 | Lee et al. | 341/144 |

(Continued)

FOREIGN PATENT DOCUMENTS

| | | |
|---|---|---|
| WO | 2005105201 | 11/2005 |
| WO | 2010126342 | 11/2010 |

OTHER PUBLICATIONS

U.S. Appl. No. 13/118,764, filed May 31, 2011, "System and Method of Establishing a Protocol for Providing Electrical Stimulation With a Stimulation System to Treat a Patient," Kaula et al.

(Continued)

*Primary Examiner* — Kristie Shingles
*Assistant Examiner* — Timothy Sowa
(74) *Attorney, Agent, or Firm* — Michael Best & Friedrich LLP (57) ABSTRACT

Systems and methods for communication between an implantable medical device and an external device. Data blocks are generated and transmitted between the implantable device and the external device. The data blocks include a first flag indicating whether the data block is a first data block in a message and when the data block is a subsequent data block in a multiple data block message. When the first flag indicates that the data block is a first data block in a message, the data block also contains a device ID, a command token, and message content. When the first flag indicates that the data block is a subsequent data block in a multiple data block message, the data block contains additional message content that is appended to message content from a previously received data block.

24 Claims, 5 Drawing Sheets

(56) References Cited

U.S. PATENT DOCUMENTS

| | | | |
|---|---|---|---|
| 7,931,598 | B2 | 4/2011 | Bodecker et al. |
| 7,940,933 | B2 | 5/2011 | Corndorf |
| 8,265,768 | B2 * | 9/2012 | Klostermann et al. .......... 607/60 |
| 8,468,372 | B2 * | 6/2013 | Johnson et al. ............... 713/300 |
| 2002/0050925 | A1 * | 5/2002 | Arms et al. .................... 340/505 |
| 2005/0192649 | A1 * | 9/2005 | Shehadeh et al. ............... 607/60 |
| 2005/0192842 | A1 * | 9/2005 | Stawski et al. ..................... 705/3 |
| 2006/0020304 | A1 | 1/2006 | Torgerson et al. |
| 2006/0173444 | A1 * | 8/2006 | Choy et al. .................. 604/891.1 |
| 2007/0049990 | A1 * | 3/2007 | Klostermann et al. .......... 607/60 |
| 2009/0018598 | A1 * | 1/2009 | Doerr et al. ..................... 607/30 |
| 2010/0013668 | A1 * | 1/2010 | Kantervik ............... 340/870.07 |
| 2010/0073127 | A1 * | 3/2010 | Fukushima .................... 340/5.6 |
| 2010/0094654 | A1 * | 4/2010 | Stewart .............................. 705/3 |
| 2010/0100203 | A1 | 4/2010 | Crivelli et al. |
| 2011/0172741 | A1 | 7/2011 | Roberts et al. |
| 2011/0179405 | A1 * | 7/2011 | Dicks et al. .................... 717/168 |
| 2011/0270025 | A1 * | 11/2011 | Fridez et al. ..................... 600/37 |
| 2012/0163481 | A1 * | 6/2012 | Ebner et al. .................... 375/259 |

OTHER PUBLICATIONS

U.S. Appl. No. 13/118,775, filed May 31, 2011, "System and Method of Establishing a Protocol for Providing Electrical Stimulation With a Stimulation System to Treat a Patient," Kaula et al.

* cited by examiner

| Byte 1 | Flag |
|---|---|
| Byte 2 | Data (1 of 13) |
| Byte 3 | Data (2 of 13) |
| Byte 4 | Data (3 of 13) |
| Byte 5 | Data (4 of 13) |
| Byte 6 | Data (5 of 13) |
| Byte 7 | Data (6 of 13) |
| Byte 8 | Data (7 of 13) |
| Byte 9 | Data (8 of 13) |
| Byte 10 | Data (9 of 13) |
| Byte 11 | Data (10 of 13) |
| Byte 12 | Data (11 of 13) |
| Byte 13 | Data (12 of 13) |
| Byte 14 | Data (13 of 13) |
| Byte 15 | FinalCheckSum |

*FIG. 2B*

| Byte 1 | Flag |
|---|---|
| Byte 2 | Data (1 of 14) |
| Byte 3 | Data (2 of 14) |
| Byte 4 | Data (3 of 14) |
| Byte 5 | Data (4 of 14) |
| Byte 6 | Data (5 of 14) |
| Byte 7 | Data (6 of 14) |
| Byte 8 | Data (7 of 14) |
| Byte 9 | Data (8 of 14) |
| Byte 10 | Data (9 of 14) |
| Byte 11 | Data (10 of 14) |
| Byte 12 | Data (11 of 14) |
| Byte 13 | Data (12 of 14) |
| Byte 14 | Data (13 of 14) |
| Byte 15 | Data (14 of 14) |

*FIG. 2C*

| Byte 1 | Flag |
|---|---|
| Byte 2 | Device ID (1 of 3) |
| Byte 3 | Device ID (2 of 3) |
| Byte 4 | Device ID (3 of 3) |
| Byte 5 | Command Token (1 of 2) |
| Byte 6 | Command Token (2 of 2) |
| Byte 7 | Data (1 of 8) |
| Byte 8 | Data (2 of 8) |
| Byte 9 | Data (3 of 8) |
| Byte 10 | Data (4 of 8) |
| Byte 11 | Data (5 of 8) |
| Byte 12 | Data (6 of 8) |
| Byte 13 | Data (7 of 8) |
| Byte 14 | Data (8 of 8) |
| Byte 15 | CheckSum |

*FIG. 2A*

| Byte 1 | Flag |
|---|---|
| Byte 2 | Data (1 of 13) |
| Byte 3 | Data (2 of 13) |
| Byte 4 | Data (3 of 13) |
| Byte 5 | Data (4 of 13) |
| Byte 6 | Data (5 of 13) |
| Byte 7 | Data (6 of 13) |
| Byte 8 | Data (7 of 13) |
| Byte 9 | Data (8 of 13) |
| Byte 10 | Data (9 of 13) |
| Byte 11 | Data (10 of 13) |
| Byte 12 | Data (11 of 13) |
| Byte 13 | Data (12 of 13) |
| Byte 14 | Data (13 of 13) |
| Byte 15 | FinalCheckSum |

*FIG. 3C*

| Byte 1 | Flag |
|---|---|
| Byte 2 | Data (1 of 14) |
| Byte 3 | Data (2 of 14) |
| Byte 4 | Data (3 of 14) |
| Byte 5 | Data (4 of 14) |
| Byte 6 | Data (5 of 14) |
| Byte 7 | Data (6 of 14) |
| Byte 8 | Data (7 of 14) |
| Byte 9 | Data (8 of 14) |
| Byte 10 | Data (9 of 14) |
| Byte 11 | Data (10 of 14) |
| Byte 12 | Data (11 of 14) |
| Byte 13 | Data (12 of 14) |
| Byte 14 | Data (13 of 14) |
| Byte 15 | Data (14 of 14) |

*FIG. 3B*

| Byte 1 | Flag |
|---|---|
| Byte 2 | Response Code |
| Byte 3 | Command Token (1 of 2) |
| Byte 4 | Command Token (2 of 2) |
| Byte 5 | Data (1 of 10) |
| Byte 6 | Data (2 of 10) |
| Byte 7 | Data (3 of 10) |
| Byte 8 | Data (4 of 10) |
| Byte 9 | Data (5 of 10) |
| Byte 10 | Data (6 of 10) |
| Byte 11 | Data (7 of 10) |
| Byte 12 | Data (8 of 10) |
| Byte 13 | Data (9 of 10) |
| Byte 14 | Data (10 of 10) |
| Byte 15 | CheckSum |

COMMUNICATION FOR IMPLANTABLE MEDICAL DEVICES

BACKGROUND

The invention relates to communication with implantable medical devices. Medical devices, such as cardiac pacemakers and implantable pulse generators of spinal cord stimulation systems are implanted beneath the skin of a human body. Occasionally, these implanted devices receive messages from or send data to an external system. Such messages can include, for example, receiving updated control parameters or sending operational history data that can then be analyzed by the external system.

SUMMARY

Data messages and commands are sent from an external system to a specific implanted medical device in order to properly monitor or implement a treatment protocol. It is important that these data messages and commands are received and processed properly by the correct implanted medical device. In environments such as medical clinics, multiple patients with implanted medical devices are present in the same location. In such situations, an implanted medical device may receive data messages and commands from multiple external devices when the messages were intended to be received by another patient's implanted medical device. If an implanted medical device responds to a message intended for a different patient's device, the results could be inconsistent with the intended treatment protocol for that patient and may be potentially dangerous to the patient.

Various embodiments of the invention provide methods and systems for two-way communication between an implanted medical device and an external system. Messages are generated by the external system and responses are generated by the implanted device in a data block format. The data blocks are generated according to a defined size and structure. Data blocks generated by the external system and received by the implanted device include device identification information indicating when the received message is to be processed or disregarded by the implanted device. The data blocks also include mechanisms for communicating larger data messages through multiple data blocks and ensuring that the data block messages were received completely and properly.

In one embodiment, the invention provides a method of communicating between an implanted device implanted in a patient and an external device external to the patient. The implanted device receives a data block of a defined size and monitors the data block for a first flag. The first flag indicates when the data block is a first data block in a message and when the data block is a subsequent data block in a multiple data block message. When the first flag indicates that the data block is a first data block in the message, the implanted device monitors the data block for a device ID and a command token indicating the type of message that is being received, and stores message content from the data block to a memory of the implanted device. When the first flag indicates that the data block is a subsequent data block in a multiple data block message, the implanted device appends message content from the data block to message content stored in the memory for a previously received data block.

In some embodiments, the method further includes monitoring the data block for a checksum value. When the first flag indicates that the data block is the first data block in the message, the implanted device compares the checksum value from the data block to a checksum value calculated by the implanted device indicative of the data in the data block. A message error is transmitted by the implanted device when the checksum value from the data block is not consistent with the calculated checksum value. When the final data block in a multiple data block message is received, the implanted device compares the checksum value from the data block to a checksum value calculated by the implanted device indicative of the data in the data block and the data in all of the previously received data blocks of the message.

In some embodiments, the method further includes comparing the device ID from the data block to one or more stored device IDs indicating external devices which are authorized to communicate with the implanted device. If the device ID from the data block does not correspond to one of the stored device IDs, then the implanted device disregards the data block.

In some embodiments, the method further includes the implanted device generating a response data block of the defined size in response to receiving the message from the external device. Generating the response data block includes setting a first flag of the response data block indicating when the response data block is a first data block in a response message and when the response data block is a subsequent data block in a multiple data block response message. When the response data block is the first data block in the response message, the implanted device includes a response code, the command token, and message data in the response date block. The response code indicates when a command in the received message has been accepted by the implanted device or rejected. The command token in the response data block is the same as the command token in the received message from the external device. When the data block is a subsequent data block in a multiple data block response message, additional response message content is included in the response data block. After the response data block is generated by the implanted device, the response data block is transmitted to the external device.

In another embodiment, the invention provides a method of communicating between an implanted device implanted in a patient and an external device external to the patient. The method includes generating, by the external device, a data block of a defined size and transmitting the data block to the implanted device. Generating the data block includes setting a first flag in the data block indicating when the data block is a first data block in a message and when the data block is a subsequent data block in a multiple data block message. When the data block is a first data block in the message, the data block includes a device ID, a command token indicating the type of message, and message content. When the data block is a subsequent data block in a multiple data block message, the data block includes additional message content.

In another embodiment, the invention provides an implantable medical device including a housing, a wireless communication module, a processor, and a memory. The memory includes instructions that, when executed by the processor, cause the implantable device to receive a data block of a defined size and monitor the data bock of a first flag. The first flag indicates when the data block is a first data block in a message and when the data block is a subsequent data block in a multiple data block message. When the first flag indicates that the data block is the first data block in the message, the instructions cause the implantable device to monitor the data block for a device ID and a command token and to store message content from the data block to the memory. When the first flag indicates that the data block is a subsequent data block in a multiple data block message, the instructions cause the implantable device to append message content from the data block to message content stored in the memory from a previously received data block.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
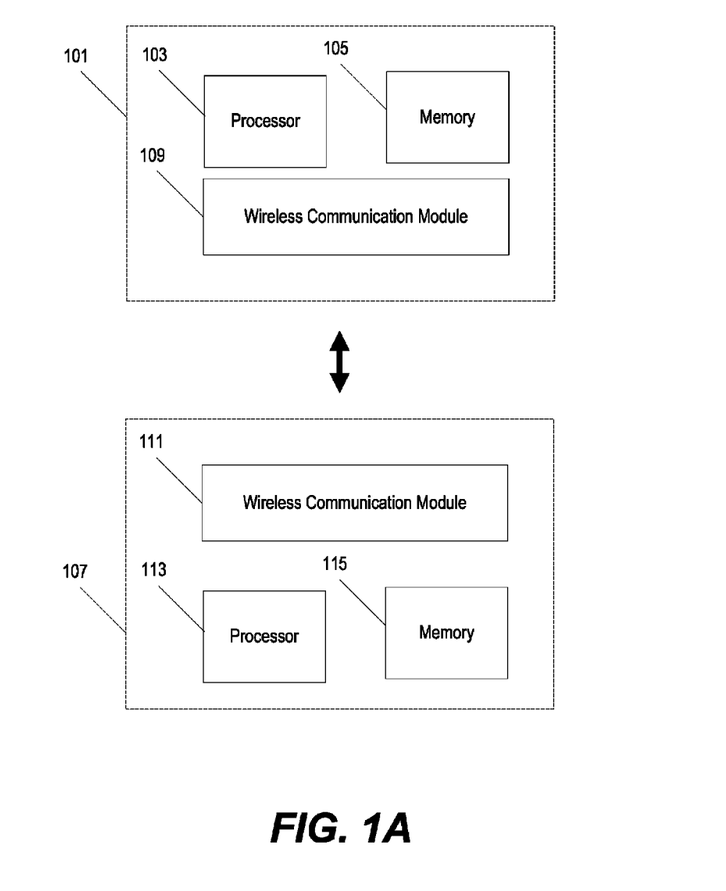
FIG. 1A is a block diagram of a system for communication between an implantable medical device and an external system.

FIG. 1A illustrates a system for communication between an implanted medical device and an external system, which may include an external device. The implanted device 101 is designed to be implanted beneath the skin of a patient. The implanted device 101 can include, for example, a cardiac pacemaker system or an implantable pulse generator for a spinal cord stimulator system. The implanted device 101 includes a processor 103 and a memory 105 positioned within a housing of the device 101. The processor 103 controls the operation of the implanted device 101 by executing instructions stored on the memory 105. In various constructions, the memory 105 can also store control parameters that govern the operation of the implanted device 101 and historical operation data indicative of past operation of the implanted device 101.

On occasion, an external device 107 is used to communicate with the implanted device 101. Such communication may be used, for example, to send operational commands to the implanted device 101, to update control parameters for the implanted device 101, or to request performance and operational data from the implanted device 101. Because the implanted device 101 is designed to be implanted beneath the skin of a patient, wired communication is not feasible. Therefore, both the implanted device 101 and the external device 107 include wireless communication modules (109 and 111, respectively) to facilitate communication between the two devices. The wireless communication modules 109, 111 in the construction illustrated in FIG. 1 include radio frequency (RF) transmitters and receivers using the Medical Implant Communication Service (MICS) band. However, in other constructions, the wireless communication can be accomplished using other communication technologies such as Bluetooth. The external device 107 also includes a processor 113 that controls the operation of the external device by executing instructions stored on a memory 115.

Figure 1B:
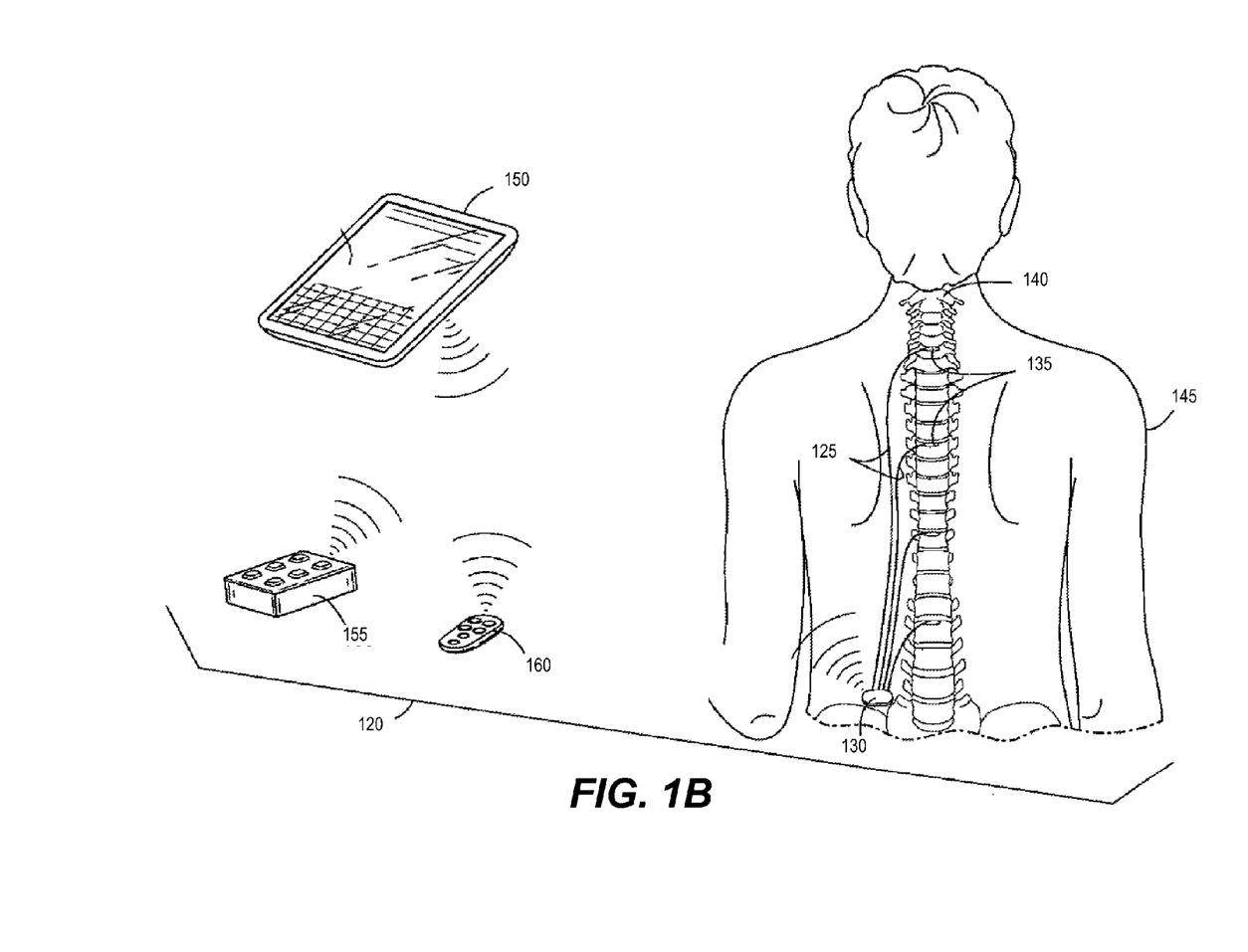
FIG. 1B is a partial perspective view of a patient using a spinal cord stimulation system including the system for communication of FIG. 1A.

FIG. 1B further illustrates one example of a spinal cord stimulation system 120. In this example, the implanted device 101 includes several implanted medical electric leads 125 connected to an implantable pulse generator (IPG) 130. The leads 125 each include electrode arrays 135 at the distal end of the base lead cable. The electrode arrays 135 include multiple electrical stimulation electrodes placed adjacent to the dura of the spine 140 of a patient 145 using an anchor. The spinal column includes the C1-C7 (cervical), T1-T12 (thoracic), L1-L5 (lumbar), and S1-S6 (sacral) vertebrae and the electrode arrays 135 may be positioned anywhere along the spine 140 to deliver the intended therapeutic effects of spinal cord electrical stimulation in a desired region of the spine 140. The electrodes of the electrode arrays 135 promote electrical stimulation to the neurons of the spine based on electrical signals generated by the IPG 130. The stimulation is provided from the IPG 130 to the electrodes via the base lead, which is connected to the IPG 130 with the proximal end of the base lead. The body of the lead can traverse through the body of the patient via the spinal column and from the spinal column through the body of the patient to the implant site of the IPG 130. The IPG 130 communicates with an external device 107. In the example of FIG. 1B, the external device 107 can include, for example, any one of a clinical programmer (CP) 150, a patient programmer and charger (PPC) 155, and a pocket (or fob) programmer (PP) 160.

Examples of implantable pulse generators and spinal cord stimulation systems are described in further detail in U.S. application Ser. No. 13/118,764, titled "SYSTEM AND METHOD OF ESTABLISHING A PROTOCOL FOR PROVIDING ELECTRICAL STIMULATION WITH A STIMULATION SYSTEM TO TREAT A PATIENT," filed on May 31, 2011 and U.S. application Ser. No. 13/118,775, also titled "SYSTEM AND METHOD OF ESTABLISHING A PROTOCOL FOR PROVIDING ELECTRICAL STIMULATION WITH A STIMULATION SYSTEM TO TREAT A PATIENT," filed on May 31, 2011, both of which are incorporated herein by references in their entirety.

The implanted medical device 101 and the external device 107 communicate according to a data block-based format. All data blocks used in the communication are of the same, defined size. The data block format used provides for communication of larger volume data message content by allowing messages to be spread across multiple data blocks. Furthermore, the data block format provides mechanisms to ensure that only complete and properly formatted messages received from approved external devices are processed by the implanted device 101.

Figure 2A:
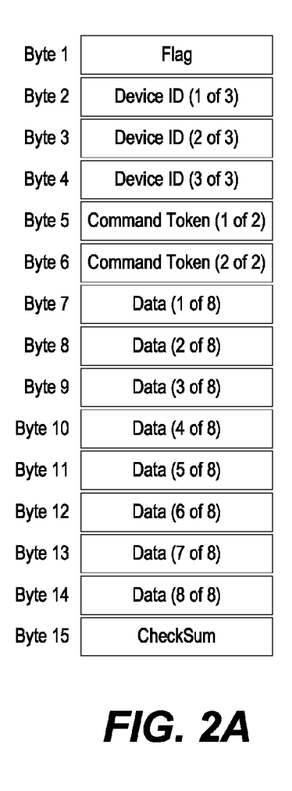
FIG. 2A is a diagram of the content of a first data block in a message received by the implantable medical device of FIG. 1 from the external system.
Figure 2B:
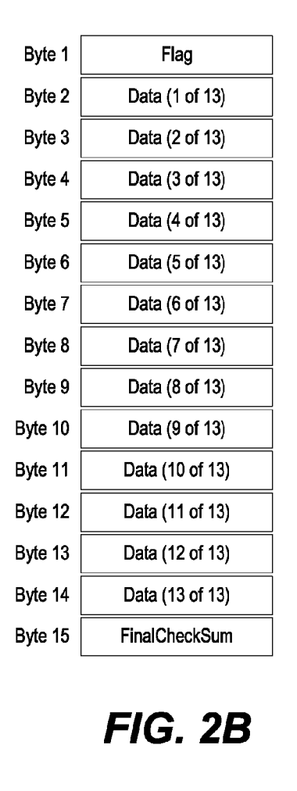
FIG. 2B is a diagram of the content of a final data block in a multiple data block message received by the implantable medical device of FIG. 1 from the external system.
Figure 2C:
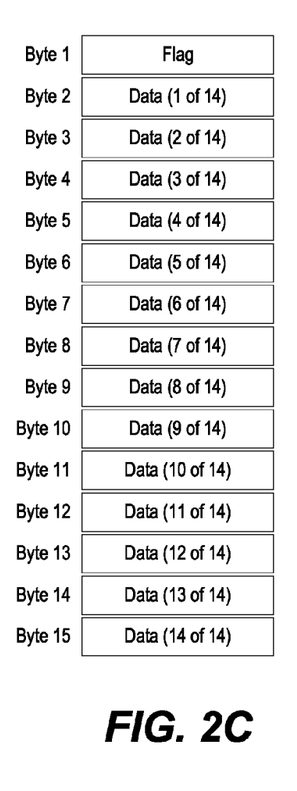
FIG. 2C is a diagram of the content of an intermediate data block in a multiple data block message received by the implantable medical device of FIG. 1 from the external system.

FIGS. 2A-2C illustrate the format of data blocks generated by the external device 107 and transmitted to the implanted device 101. Each data block in a message sent according to this example is fifteen bytes in size. However, the data blocks can be larger or smaller in other constructions. The first byte of every data block includes a flag that indicates whether the data block is the first data block in a message. A value of "1" in the first byte indicates that the data block either contains a single data block message or is the first data block of a multiple data block message. A value of "0" indicates that the data block is either a subsequent data block in a multiple data block message or was sent and received in error.

The data block of FIG. 2A is the data block format used for a single data block message or for the first data block of a multiple data block message. As described above the flag in Byte 1 contains a value of "1" to indicate such. The next three bytes in the data block (bytes 2-4) contain a device identifier ("device ID"). The device ID in this example identifies the external device 107 sending the message. Upon receiving the message and verifying the correctness of the bytes received, the implanted device 101 checks the device ID against a stored list of one or more external devices that are approved to communicate with the implanted device. This mechanism ensures that the implanted device 101 responds only to commands that were intended for the implanted device 101. In other constructions, the device ID defined in bytes 2-4 of the data block of FIG. 2A identify the implanted device 101 for which the message is intended. In such embodiments, the implanted device 101 will only process messages that identify the specific implanted device 101 in the device ID bytes.

Bytes 5 and 6 in the data block of FIG. 2A define a command token. The command token identifies the command being sent. Bytes 7-14 include message data content. When the implanted device 101 receives a message including the data block of FIG. 2A, the command token instructs the implanted device 101 how to process the message data content. In some examples, the implanted device 101 is also able to determine how many data blocks will be included in the message based on the command token.

The last byte in the data block of FIG. 2A (byte 15) contains a checksum value. To ensure accuracy of the message included in the data block, the implanted device 101 calculates a checksum value based on the previous fourteen bytes in the data block of FIG. 2A (including the flag byte, the device ID, and the command token) and compares the calculated checksum value to the checksum value in byte 15 of the data block. The checksum value is calculated by adding all bytes of the data block together and ignoring any overflow. In other constructions, other checksum calculation techniques may be implemented.

If the number of bytes required for the message data content is greater than eight, the message can be transmitted through multiple data blocks. FIG. 2B illustrates a final data block in a multiple data block message. As described above, the first byte in the data block of FIG. 2B is a flag byte. The value of the flag byte in the data block of FIG. 2B is set to "0" to indicate that the data block is a subsequent data block in a multiple data block message. Additional message content is stored in bytes 2-14 of the data block. This additional message content is combined with message content from the first data block (FIG. 2A). The last byte in the data block of FIG. 2B (byte 15) is a final checksum value. When the implanted device 101 receives the final data block, it calculates a final checksum value indicative of all of the previous bytes in all of the data blocks in the multiple data block message—including the first data block and the checksum value in byte 15 of the first data block (FIG. 2A). The implanted device 101 verifies the accuracy of the entire message by comparing this calculated checksum value to the final checksum value in byte 15 of the final data block.

If the number of bytes required for the message data content is greater than 21, the message can be transmitted through three or more data blocks. FIG. 2C illustrates an intermediate data block in a message sent through three or more data blocks. Again, the first byte in the intermediate data block is a flag byte, the value of which is set to "0" to indicate that the data block is not the first data block in a multiple data block message. The remaining bytes in the data block (bytes 2-15) all contain additional message data content that, when received by the implanted device 101, is combined with message content from previously received data blocks.

For example, a message that requires 35 bytes for the message data content would be sent using three data blocks. The first data block would be of the format illustrated in FIG. 2A. The value of the flag byte would be set to "1" to indicate that it is the first data block in a message. The first data block would also include the device ID of the external device 107 that generated and sent the message. It would also include a command token, the first eight bytes of message data content, and a checksum value indicative of the data in the previous fourteen bytes of the first data block. The second data block would be an intermediate data block of the format illustrated in FIG. 2C. The value of the flag byte of the second data block would be set to "0" to indicate that the second data block is a subsequent data block of a multiple data block message. The second data block would also include the next fourteen bytes of message data content. The third and final data block in the three data block message would be of the format illustrated in FIG. 2B. The flag byte again would be set to "0" to indicate that the third data block is a subsequent data block of a multiple data block message. The third data block would also include the next thirteen bytes of message data content. The last byte (byte 15) of the third data block would include a checksum value indicative of the data in the previous fourteen bytes of the third data block and all of the bytes of the first and second data blocks.

In this example, the data block message format is used to implement a command-response form of communication between the external device 107 and the implanted device 101. After receiving a complete message from the external device 107, the implanted device 101 generates and transmits a response message. The format of the response message is slightly different from the format of the initial command message. However, the response message is also transmitted through a data block of the same size as the command message—in this case fifteen bytes.

Figure 3A:
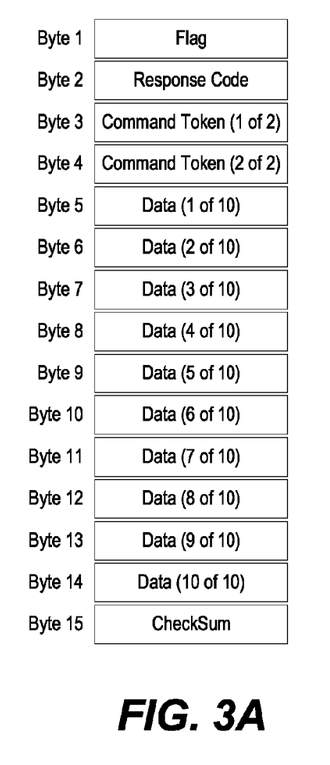
FIG. 3A is a diagram of the content of a first data block in a response message sent by the implantable medical device of FIG. 1 to the external system.
Figure 3B:
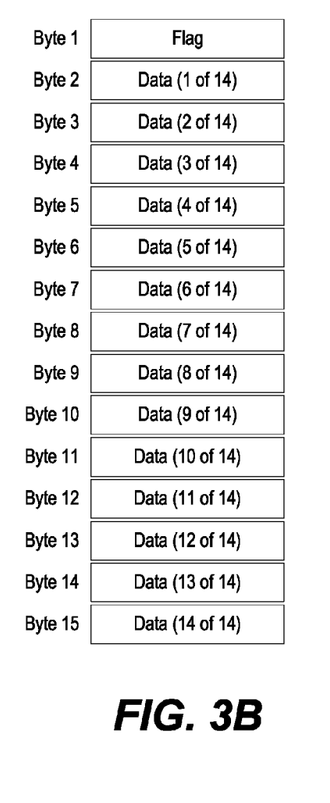
FIG. 3B is a diagram of the content of an intermediate data block in a multiple data block response message sent by the implantable medical device of FIG. 1 to the external system.
Figure 3C:
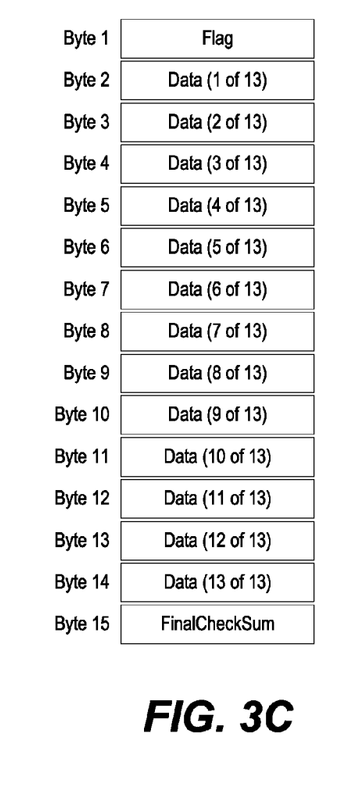
FIG. 3C is a diagram of the content of a final data block in a multiple data block response message sent by the implantable medical device of FIG. 1 to the external system.

FIGS. 3A-3C illustrate the format of the response message. Like the command messages, the first byte of each data block of the response message is a flag byte. The value of the flag byte is set to "1" to indicate when the data block includes a single data block response message or a first data block in a multiple data block response message. The value of the flag byte is set to "0" to indicate when the data block is a subsequent data block in a multiple data block response message.

The data block of FIG. 3A illustrates the format of a single data block response message and a first data block of a multiple data block response message. As described above, the first byte is a flag byte, the value of which is set to "1." The second byte is a response code. The response code indicates whether the command from the command message received by the implanted device 101 was processed by the implanted device 101. The next two bytes (bytes 3 and 4) include the same command token that was included in bytes 2 and 3 of the first data block of the command message (FIG. 2A). Bytes 5-14 include response parameter data. The response code and the command token are used by the external device 107 to determine which bytes of the data block include response parameter data and how many data blocks will be included in the response message.

The final byte (byte 15) of the first data block of the response message includes a checksum value. Like the first data block of the command message described above (FIG. 2A), the checksum value of the first data block of the response message is also indicative of the content in the previous bytes (bytes 1-14) of the first data block of the response message. As such, when the external device 107 receives a first data block of a response message, the external device 107 calculates a checksum value based on the data in bytes 1-14 and compares the calculates checksum value to the checksum value in byte 15 to verify the accuracy of the message content.

FIG. 3B illustrates an intermediate data block of a response message that includes at least three data blocks. The first byte in the intermediate data block includes a flag, the value of which is set to "0" to indicate that the data block is a subsequent data block in a multiple data block message. The remaining bytes of the intermediate data block include the next fourteen bytes of response parameter data for the response message.

FIG. 3C illustrates a final data block of a response message that includes at least two data blocks. The first byte in the final data block includes a flag, the value of which is set to "0" to indicate that the data block is a subsequent data block in a multiple data block message. Bytes 2-14 include the last fourteen bytes of response parameter data for the response message. The last byte of the final data block (byte 15) includes a final checksum value. Like in the final data block of the command message described above (FIG. 3B), the final checksum value is indicative of the content in the previous bytes (bytes 1-14) of the final data block and all of the bytes in the previous data blocks of the multiple data block response message. As such, when the external device 107 receives the final data block of a response message, the external device 107 calculates a final checksum value based on the data in bytes 1-14 of the final data block and all of the bytes of the previous data blocks in the response message. The external device 107 then compares the calculated final checksum value to the checksum value in byte 15 of the final data block to verify the accuracy of the response message content.

As described above, the implanted device 101 can detect an error in the format of a message received from an external device based on the checksum value. Furthermore, the implanted device 101 can determine when the device ID of the external device sending the message is not recognized. In either case, the implanted device 101 can either ignore the defective message or can send a response message indicating that the message was defective and was not processed by the implanted device 101. When the external device 107 receives such an "error" message from the implanted device 101, the external device will correct the message and resend. Alternatively, the external device 107 monitors for a response message and resends the command message if a response is not received within a defined period of time.

Figure 4:
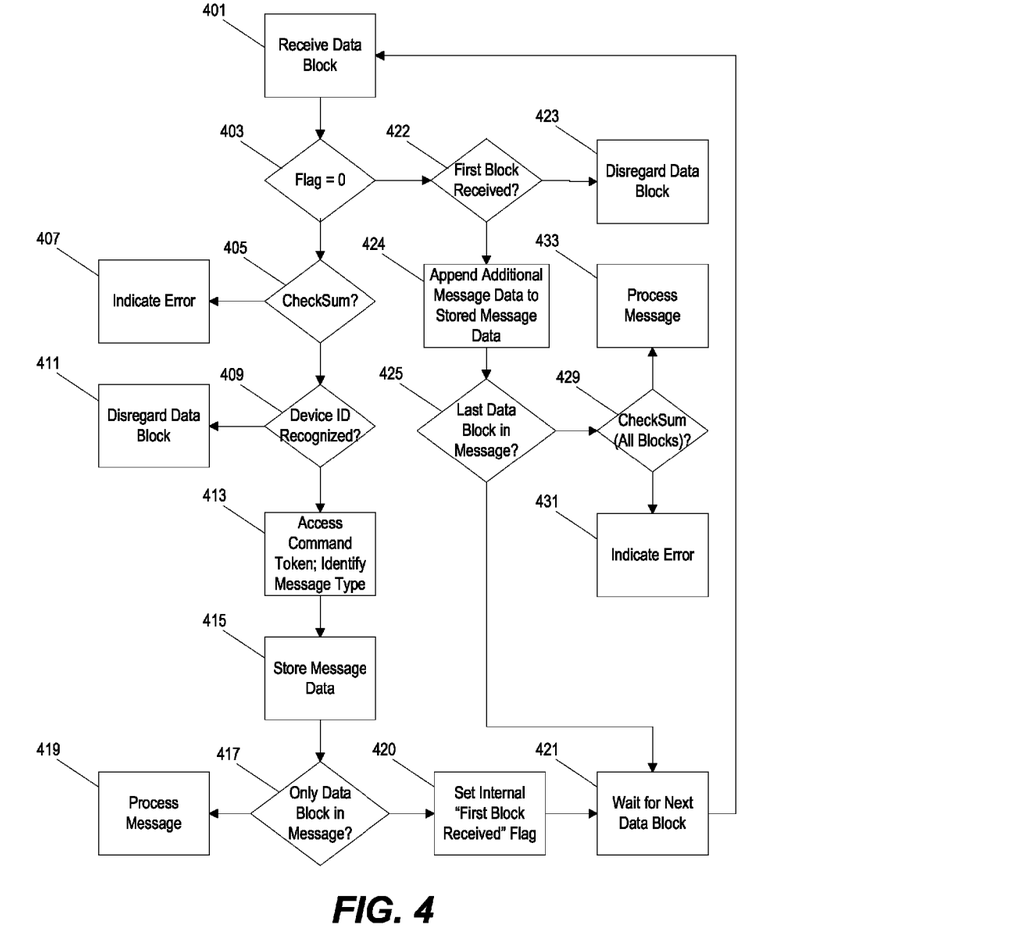
FIG. 4 is a flowchart of a method of analyzing a data block received by the implantable device of FIG. 1 from the external system.

FIG. 4 illustrates how the implanted device 101 receives and processes data blocks received from the external device 107 according to the format described above in reference to FIGS. 2A-2C. The implanted device 101 begins by receiving a data block through the wireless communication module 109 (step 401). The implanted device 101 monitors the first byte (i.e., the flag byte) of the received data block to determine whether the data block is a first data block of a message (step 403). If the flag byte indicates that the data block is a first data block of a message, the implanted device verifies the accuracy of the received message by comparing the checksum value in byte 15 of the data block to a calculated checksum value (step 405). If the calculated checksum value is not consistent with the checksum value in byte 15, the implanted device 101 either sends a response message indicating the error condition or disregards the data block (step 407).

If the checksum values verify the accuracy of the message content in the first data block, the implanted device 101 then checks the device ID in bytes 2-4 to determine whether the external device sending the message is authorized to send commands to the implanted device 101 (step 409). If the device ID is not recognized by the implanted device 101, the command message is not processed. The implanted device 101 then either sends a response message indicating the problem or disregards the message (step 411).

If the device ID is recognized, the implanted device 101 accesses the command token in bytes 5-6 and identifies the type of message/command (step 413). The implanted device 101 stores the message content data from bytes 7-14 to an internal memory. As noted above, the implanted device 101 is able to identify the length and format of the message content data based on the command token and, in some constructions, is able to determine how many data blocks will be included in the message. If the first data block is the only data block in the message (step 417), the implanted device 101 processes the command message (step 419). However, if other data blocks are to be received, the implanted device 101 sets an internal flag indicating that the implanted device 101 has received a first data block in a multiple data block message (step 420) and waits for additional data blocks before processing the message (step 421).

When the flag in the first byte of the data block indicates that the data block is a subsequent data block in a multiple data block message (step 403), the implanted device 101 begins by verifying that the implanted device 101 has received a first data block for the message (step 422). If the implanted device 101 receives a "subsequent" data block before receiving the first data block in the message (as indicated by the internal "first block received" flag), the "subsequent" data block is disregarded (step 423).

If the internal flag indicates that a first data block was received before the subsequent data block (step 422), the implanted device 101 appends the additional message data from the data block (bytes 2-15 in an intermediate data block and bytes 2-14 in a final data block) to stored message data from previously received data blocks (step 424). As described above, the implanted device 101 is able to determine the number of data blocks to expect in a message based on the command token. As such, the implanted device is able to determine if the received "subsequent" data block is the final data block in the message (step 425). If the data block is not the final data block in the message, the implanted device 101 continues to wait for the remaining data blocks before processing the message/command (step 421). However, if the data block is the final data block in a multiple data block message, the implanted device 101 calculates a final checksum based on the data from all of the data blocks in the message and compares the calculated final checksum to the final checksum value in byte 15 of the final data block (step 429). If the final checksum values are not consistent, the implanted device either sends a response message indicating the error or disregards the message (step 431). If the final checksum values are consistent, the implanted device 101 processes the multiple data block message.

The external device 107 processes received response messages according to a similar method. After receiving a response message, the external device checks the first flag and, if appropriate, the checksum value. However, the response message will not include a device ID. Furthermore, the external device 107 will monitor first data blocks of response messages for a response code and a command token to determine how to process the response message.

Thus, the invention provides, among other things, systems and methods for communication between an implanted device implanted in a patient and an external device external to the patient. The communication methods utilize data blocks of a defined size to transmit messages and responses. The communication format accommodates messages of varying sizes by extending a single message across multiple data blocks. Furthermore, the communication format allows the implanted device to identify the external device that has sent the message and disregard messages received from unapproved external devices.

The systems and methods described above are exemplary. Other constructions and embodiments are possible. For example, in the methods described above, only the first and last data blocks in multiple data block messages include checksum values. In other constructions, all data blocks may include a checksum value indicative of the previous bytes in the data block and all of the bytes in all previously received/transmitted data blocks. Furthermore, in other constructions, the data blocks of a multiple data block message may identify the order of the data blocks. For example, the flag byte may identify the placement of the data block in the sequence of multiple data blocks instead of only identifying whether the data block is the first data block of a message. Additionally, in other constructions, information such as the device ID can be included in all of the data blocks in a multiple data block message instead of only the first data block. Various features and advantages of the invention are set forth in the following claims.

What is claimed is:

1. A method of communicating between an implanted device implanted in a patient and an external device external to the patient, the method comprising:
    receiving, by the implanted device, a first data block of a defined size;
    monitoring the first data block for a first flag indicating whether the first data block is an initial data block in a message or a subsequent data block in a multiple data block message;
    when the first flag indicates that the first data block is the initial data block in the message, monitoring the first data block for a fixed device ID,
        comparing the fixed device ID from the first data block to one or more stored fixed device IDs, the one or more stored fixed device IDs each uniquely identifying a specific external device,
        identifying a device sending the first data block as a first authorized device when the fixed device ID from the first data block matches a stored fixed device ID, of the one or more stored fixed device IDs, corresponding to the first authorized device;
    when the first flag indicates that the first data block is the initial data block in the message, monitoring the first data block for a command token indicating the type of message that is being received;
    when the first flag indicates that the first data block is the initial data block in the message, storing message content from the first data block to a memory of the implanted device;
    when the first flag indicates that the first data block is a subsequent data block in a multiple data block message, appending message content from the first data block to message content stored in the memory from a previously received data block;
    receiving, by the implanted device, a second data block of the defined size;
    monitoring the second data block for a first flag indicating whether the second data block is an initial data block in a second message or a subsequent data block in the same message as the first data block; and
    when the first flag of the second data block indicates that the second data block is the initial data block in a second message, monitoring the second data block for a fixed device ID,
        comparing the fixed device ID from the second data block to the one or more stored fixed device IDs,
        identifying the device sending the second data block as the first authorized device when the fixed device ID from the second data block matches the stored fixed device ID corresponding to the first authorized device, and
        identifying the device sending the second data block as a second authorized device when the fixed device ID from the second data block matches a stored fixed device ID, of the one or more stored fixed device IDs, corresponding to the second authorized device.

2. The method of claim 1, further comprising:
    monitoring the first data block for a checksum value; and
    when the first flag indicates that the first data block is the initial data block in the message, comparing the checksum value from the first data block to a checksum value calculated by the implanted device indicative of the data in the first data block.

3. The method of claim 2, further comprising transmitting, from the implanted device, a message error when the checksum value from the first data block is not consistent with the calculated checksum value.

4. The method of claim 2, further comprising:
    when the first flag indicates that the first data block is a subsequent data block in a multiple data block message, comparing the checksum value from the first data block to a checksum value calculated by the implanted device, the checksum value being indicative of the data in the first data block and data in at least one previously received data block of the message.

5. The method of claim 4, wherein, when the first flag indicates that the first data block is a subsequent data block in a multiple data block message, comparing the checksum value from the first data block to a checksum value calculated by the implanted device, the checksum value being indicative of the data in the first data block and data in all of the previously received data blocks of the message.

6. The method of claim 2, wherein the implanted device monitors the first data block for the checksum value by monitoring a last byte of the first data block.

7. The method of claim 1,
    wherein the implanted device monitors the first data block for the first flag by monitoring a first byte in the first data block,
    wherein, when the first flag indicates that the first data block is the first data block in the message, the implanted device monitors the first data block for the fixed device ID by monitoring a second byte, a third byte, and a fourth byte in the first data block, and
    wherein, when the first flag indicates that the first data block is the initial data block in the message, the implanted device monitors the first data block for the command token by monitoring a fifth byte and a sixth byte in the first data block.

8. The method of claim 1, further comprising disregarding the first data block when the first flag indicates that the first data block is a subsequent data block in a multiple data block message and when the implanted device has not received a previous data block in the multiple data block message.

9. The method of claim 1, wherein receiving, by the implanted device, a first data block of a defined size includes
receiving a radio-frequency signal by a communication module included in the implanted device, and
extracting the first data block from the radio-frequency signal.

10. The method of claim 1, further comprising:
generating, by the implanted device, a response data block of the defined size in response to receiving the message from the external device, wherein generating the response data block includes
setting a first flag of the response data block indicating whether the response data block is an initial data block in a response message or a subsequent data block in a multiple data block response message,
when the response data block is the initial data block in the response message, including a response code in the response data block indicating when a command in the message received from the external device has been accepted by the implanted device and when the command in the message received from the external device has been rejected by the implanted device,
when the response data block is the initial data block in the response message, including the command token from the message received from the external device in the response data block,
when the response data block is the initial data block in the response message, including response message data in the response data block, and
when the response data block is a subsequent data block in a multiple data block response message, including additional response message content in the response data block; and
transmitting, by the implanted device, the response data block.

11. The method of claim 10, wherein generating a response data block of a defined size further includes
including the first flag of the response data block in a first byte of the response data block,
when the response data block is the initial data block in the response message, including the response code in a second byte of the response data block,
when the response data block is the initial data block in the response message, including the command token in a third byte and a fourth byte of the response data block,
when the response data block is the initial data block in the response message, including a response checksum value in the last byte of the response data block, wherein the response checksum value is indicative of the data in the response data block, and
when the response data block is the initial data block in the response message, including response message data in the remaining bytes of the response data block.

12. The method of claim 1, further comprising:
disregarding the first data block if the fixed device ID from the first data block does not correspond to one of the stored fixed device IDs; and
disregarding the second data block if the fixed device ID from the second data block does not correspond to one of the stored fixed device IDs.

13. A method of communicating between an implanted device implanted in a patient and an external device external to the patient, the method comprising:
generating, by the external device, a first data block of a defined size, wherein generating the first data block includes
setting a first flag in the first data block indicating whether the first data block is an initial data block in a message or a subsequent data block in a multiple data block message,
when the first data block is an initial data block in the message, including a fixed device ID in the first data block,
wherein the fixed device ID is a pre-assigned ID that uniquely identifies the external device, and
wherein the implanted device stores a list of approved device IDs, each uniquely identifying a different authorized device, and only responds to messages sent from authorized devices;
when the first data block is the initial data block in the message, including a command token in the first data block indicating the type of message,
when the first data block is the initial data block in the message, including message content in the first data block, and
when the first data block is a subsequent data block in a multiple data block message, including additional message content in the first data block;
transmitting, by the external device, the first data block;
generating, by the external device, a second data block of the defined size, wherein, when the second data block is an initial data block in a second message, generating the second data block includes including the fixed device ID in the second data block, wherein the fixed device ID in the second data block is the same as the fixed device ID in the first data block; and
transmitting, by the external device, the second data block.

14. The method of claim 13, wherein generating a first data block of a defined size further includes
calculating a checksum value, and
including the checksum value in the first data block,
wherein, when the first data block is an initial data block in the message, the calculated checksum value is indicative of the data in the first data block.

15. The method of claim 14, wherein, when the first data block is a subsequent data block in a multiple data block message, the calculated checksum value is indicative of the data in the first data block and data in at least one previously transmitted data block of the message.

16. The method of claim 14, wherein, when the first data block is a last data block in a multiple data block message, the calculated checksum value is indicative of the data in the first data block and data in all of the previously received data blocks of the message.

17. The method of claim 14, wherein generating a first data block of a defined size further includes including the calculated checksum value in a last byte of the first data block.

18. The method of claim 13, wherein generating a first data block of a defined size further includes
including the first flag in a first byte of the first data block,
when the first data block is the initial data block in the message, including the fixed device ID in a second byte, a third byte, and a fourth byte of the first data block, and when the first data block is the initial data block in the message, including the command token in a fifth byte and a sixth byte of the first data block.

19. The method of claim 13, further comprising:
receiving, by the external device, a response data block of a defined size;
monitoring the response data block for a first flag indicating whether the response data block is an initial data block in a response message or a subsequent data block in a multiple data block response message;
when the first flag of the response data block indicates that the response data block is the initial data block in the response message, monitoring the response data block for a response code, the response code indicating when a command in the message transmitted by the external device has been accepted by the implanted device and when the command in the message transmitted by the external device has been rejected by the implanted device;
when the first flag of the response data block indicates that the response data block is the initial data block in the response message, monitoring the response data block for a command token and confirming that the command token in the response data block corresponds to the command token in the message sent by the external device;
when the first flag of the response data block indicates that the response data block is the initial data block in the response message, storing response message data from the response data block to a memory of the external device; and
when the first flag of the response data block indicates that the response data block is a subsequent data block of a multiple data block response message, appending response message data from the response data block to response message data stored in the memory of the external device from a previously received response data block.

20. The method of claim 19, further comprising:
monitoring the last byte of the response data block for a checksum value; and
comparing the checksum value from the response data block to a checksum value calculated by the external device indicative of the data in the response data block,
wherein the monitoring the response data block for the first flag includes monitoring a first byte of the response data block,
wherein, when the first flag of the response data block indicates that the response data block is the initial data block in the response message, the monitoring the response data block for the response code includes monitoring a second byte of the response data block,
wherein, when the first flag of the response data block indicates that the response data block is the initial data block in the response message, the monitoring the response data block for the command token includes monitoring a third byte and a fourth byte of the response data block, and
wherein, when the first flag of the response data block indicates that the response data block is the initial data block in the response message, the storing response message data from the response data block to a memory of the external device includes monitoring the remaining bytes of the response data block for response message data.

21. An implantable device comprising:
a housing;
a wireless communication module within the housing;
a processor within the housing; and
a memory storing executable instructions that, when executed by the processor, cause the implantable device to
receive a first data block of a defined size,
monitor the first data block for a first flag indicating whether the first data block is an initial data block in a message or a subsequent data block in a multiple data block message,
when the first flag indicates that the first data block is the initial data block in the message, monitor the first data block for a fixed device ID,
compare the fixed device ID from the first data block to a stored list of a plurality of fixed device IDs, the fixed device IDs from the stored list of the plurality of fixed device IDs each uniquely representing a specific external device,
identify a device sending the first data block as a first authorized device when the fixed device ID from the first data block matches a first stored fixed device ID from the stored list of the plurality of fixed device IDs, the first stored fixed device ID corresponding to the first authorized device,
when the first flag indicates that the first data block is the initial data block in the message, monitor the first data block for a command token indicating the type of message that is being received,
when the first flag indicates that the first data block is the initial data block in the message, store message content from the first data block to the memory,
when the first flag indicates that the first data block is a subsequent data block in a multiple data block message, append message content from the first data block to message content stored in the memory from a previously received data block,
receive a second data block of the defined size,
monitor the second data block for a first flag indicating whether the second data block is an initial data block in a second message or a subsequent data block in the same message as the first data block, and
when the first flag of the second data block indicates that the second data block is the initial data block in a second message, monitor the second data block for a fixed device ID,
compare the fixed device ID from the second data block to the one or more stored fixed device IDs,
identify the device sending the second data block as the first authorized device when the fixed device ID from the second data block matches the first stored fixed device ID, and
identify the device sending the second data block as a second authorized device when the fixed device ID from the second data block matches a second stored fixed device ID from the stored list of fixed device IDs, wherein the second stored fixed device ID is different from the first stored fixed device ID, and wherein the second stored fixed device ID corresponds to the second authorized device.

22. The implantable device of claim 21, wherein the instructions, when executed by the processor, further cause the implantable device to
monitor the first data block for a checksum value,
when the first flag indicates that the first data block is the initial data block in the message, compare the checksum value from the first data block to a checksum value calculated by the implantable device indicative of the data in the first data block, and when the first flag indicates that the first data block is a subsequent data block in a multiple data block message, compare the checksum value from the first data block to a checksum value calculated by the implantable device indicative of the data in the first data block and data in at least one previously received data block of the message.

23. The implantable device of claim 22 wherein the instructions, when executed by the processor, cause the implantable device to monitor the first data block for the first flag by monitoring a first byte in the first data block, when the first flag indicates that the first data block is the initial data block in the message, monitor the first data block for the fixed device ID by monitoring a second byte, a third byte, and a fourth byte in the first data block, when the first flag indicates that the first data block is the initial data block in the message, monitor the first data block for the command token by monitoring a fifth byte and a sixth byte in the first data block, monitor the first data block for the checksum value by monitoring a last byte in the first data block, and monitor the first data block for message content by monitoring other bytes in the first data block.

24. The implantable device of claim 21, wherein the instructions, when executed by the processor, cause the implantable device to disregard the first data block if the fixed device ID from the first data block does not correspond to one of the stored fixed device IDs, and disregard the second data block if the fixed device ID from the second data block does not correspond to one of the stored fixed device IDs.

* * * * *